United States Patent [19]
Lipsky et al.

[11] Patent Number: 4,976,923
[45] Date of Patent: Dec. 11, 1990

[54] SAMPLE CONTAINER

[75] Inventors: Milton H. Lipsky, West Greenwich; Andrew Rosner, Barrington, both of R.I.

[73] Assignee: Rhode Island Hospital, Providence, R.I.

[21] Appl. No.: 351,456

[22] Filed: May 12, 1989

[51] Int. Cl.$^5$ ............... G01N 21/00; G01N 33/48; G01N 33/493
[52] U.S. Cl. .................... 422/58; 422/55; 422/56; 422/61; 422/68.1; 436/165; 436/810
[58] Field of Search ............ 422/58, 61, 68, 55, 422/56, 57; 436/1, 165, 810; 73/863.52, 864.91; 604/403, 404; 356/407, 421, 422, 423, 412

[56] References Cited

U.S. PATENT DOCUMENTS

| | | | |
|---|---|---|---|
| 1,125,078 | 1/1915 | Dunn | 356/423 |
| 2,027,816 | 1/1936 | Drucker | 356/412 |
| 2,370,683 | 6/1940 | Palma . | |
| 3,774,455 | 11/1973 | Seidler et al. . | |
| 3,786,510 | 1/1974 | Hodges . | |
| 3,815,769 | 6/1974 | Rapoza et al. . | |
| 3,918,433 | 11/1975 | Fuisz . | |
| 4,046,138 | 9/1977 | Libman et al. | 73/863.52 |
| 4,473,530 | 9/1984 | Villa-Real . | |
| 4,591,062 | 5/1986 | Sandhaus | 422/58 |

FOREIGN PATENT DOCUMENTS

| | | | |
|---|---|---|---|
| 2401892 | 7/1975 | Fed. Rep. of Germany | 422/55 |
| 2729283 | 2/1979 | Fed. Rep. of Germany . | |
| 225337 | 7/1985 | Fed. Rep. of Germany . | |
| 0238763 | 11/1985 | Japan | 422/56 |

Primary Examiner—Robert J. Warden
Assistant Examiner—Kimberly A. Trautman

[57] ABSTRACT

A fluid testing apparatus including a specimen cup and a cover having a reagent portion which is color sensitive to an analytical characteristic.

3 Claims, 1 Drawing Sheet

SAMPLE CONTAINER

FIELD OF THE INVENTION

The invention relates to testing fluid samples.

SUMMARY OF THE INVENTION

It is known to contain a fluid sample in a specimen cup and to test the fluid sample by placing into it a dipstick having reagent portions which are color sensitive to an analytical characteristic of the fluid sample.

SUMMARY OF THE INVENTION

It has been discovered that a specimen cup with a cover having portions which are color sensitive to an analytical characteristic provides a fluid testing apparatus which is safe and sanitary.

BRIEF DESCRIPTION OF THE DRAWING

The attached drawing illustrates the preferred embodiment, the structure and operation of which is then described.

The FIGURE shows a fluid testing apparatus according to the present invention.

DESCRIPTION OF THE INVENTION

Figure 1:
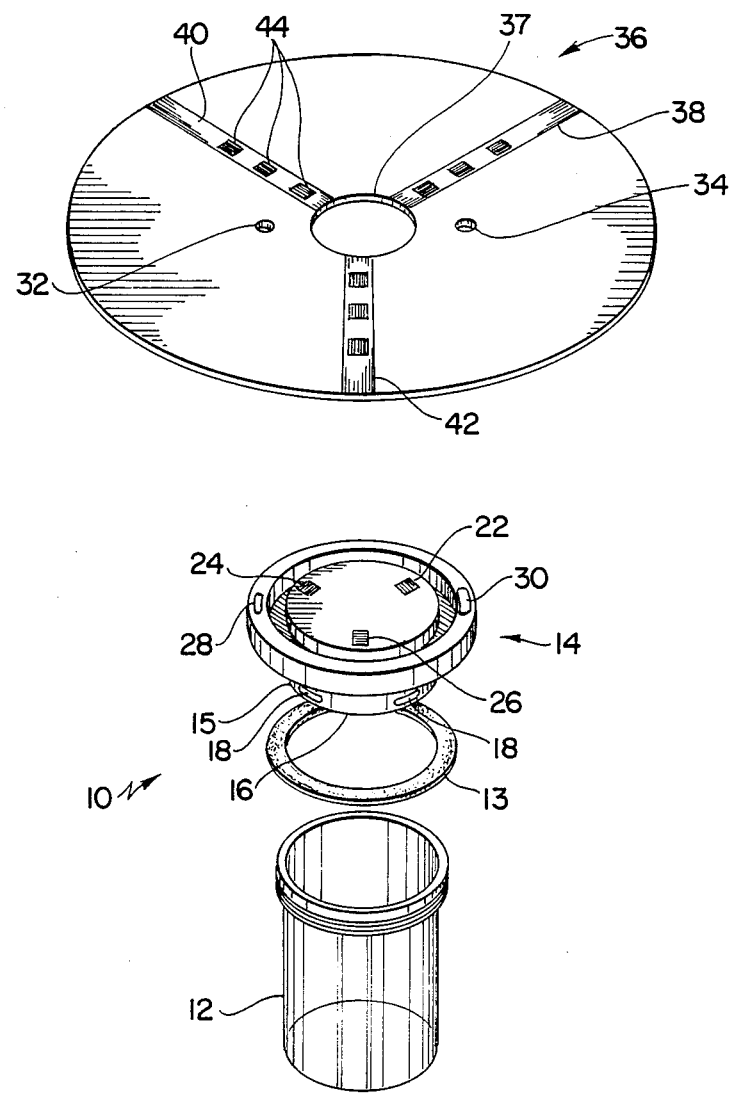

Fluid testing apparatus 10 includes specimen cup 12 to which cover assembly 14 is threadedly mated, where gasket 13 is located between cup 12 and cover assembly 14. Cover assembly 14 includes interior cover wall 15 to which plastic sheet 16 is secured, wherein the outside diameter of interior wall 15 is less than the inside diameter of cup 12. Four holes 18 (two of which are shown) are positioned at 90° intervals, along the interior wall edge which is contiguous to sheet 16.

Cover assembly 14 also includes a plurality of reagent portions 22, 24, 26 which are color sensitive to a respective plurality of analytical characteristics. Cover 14 also includes a plurality of uniquely shaped protrusions 28, 30 which mate with respective holes 32, 34 of nomogram 36. Nomogram 36 also includes hole 37 through which reagent portions 22, 24, 26 may be viewed and a plurality of axially extending color strips 38, 40, 42 having a plurality of differently colored portions 44 where the different colors signify different results to the analytical characteristics. Color strips 38, 40, 42 correspond to respective reagent portions 22, 24, 26 when protrusions 28, 30 mate with holes 32, 34.

Specimen cup 12 is filled with a test fluid (e.g., urine) and then cover assembly 14 is attached. Plastic sheet 16 prevents the test fluid from contacting portions 22, 24, 26 before commencing testing. To commence testing, cup 12 is inverted to allow fluid to flow through holes 18 to reagent portions 22, 24, 26. Cup 12 is then righted and nomogram 36 is mated with cover 14. Colored reagent portions 22, 24, 26 are compared to respective color strips 38, 40, 42 at the appropriate time. Thus, fluid testing apparatus 10 efficiently and safely tests fluid samples without exposing the operator to potentially harmful fluid samples. Additionally, because each cover could be individually sealed, the use of desiccants is not needed to preserve the reagent portions.

Other embodiments are within the following description.

Nomogram 36 may include descriptions of the analytical characteristics of reagent portions 22, 24, 26 as well as instructions for performing the tests, e.g., instructions regarding at what time to compare reagent portions 22, 24, 26 to strips 38, 40, 42.

Additionally, a machine could be used to automatically read the reagent portions, where protrusions 28, 30 are used to correctly position fluid testing apparatus 10 within the machine.

What is claimed is:

1. A fluid testing apparatus comprising:
   a specimen cup for receiving a fluid specimen therein,
   a cover assembly which is receivable and securable in covering relation on said specimen cup so that it cooperates therewith to define an enclosed area,
   said cover assembly further including an isolation chamber formed therein for containing a reagent portion,
   said isolation chamber depending from said cover assembly so that said isolation chamber is located in said enclosed area when said cover assembly is received on said specimen cup,
   said isolation chamber including a peripheral sidewall portion having a plurality of preformed apertures therein which open into an interior isolation area, and
   said reagent portion being disposed in said interior isolation area and being color sensitive to a predetermined analytical characteristic for testing said fluid specimen once the latter has passed through said apertures into said interior isolation area.

2. The fluid testing apparatus of claim 1 wherein said cover assembly includes a plurality of reagent portions, said reagent portions being sensitive to a plurality of analytical characteristics.

3. The apparatus of claim 1 wherein said reagent portion is visible without exposing an operator to said test fluid.

* * * * *

UNITED STATES PATENT AND TRADEMARK OFFICE
CERTIFICATE OF CORRECTION

PATENT NO. : 4,976,923
DATED : Dec. 11, 1990
INVENTOR(S) : Milton H. Lipsky and Andrew Rosner It is certified that error appears in the above-identified patent and that said Letters Patent is hereby corrected as shown below:

column 1, line 7, change "SUMMARY OF THE INVENTION" to --BACKGROUND OF THE INVENTION--.

Signed and Sealed this

Thirteenth Day of April, 1993

Attest:

STEPHEN G. KUNIN

*Attesting Officer*      *Acting Commissioner of Patents and Trademarks*